United States Patent [19]
Batts et al.

[11] Patent Number: 5,855,899
[45] Date of Patent: Jan. 5, 1999

[54] MATERIAL METHOD AND APPARATUS FOR INHIBITING MICROBIAL GROWTH IN AN AQUEOUS MEDIUM

[75] Inventors: Gregory Nigel Batts, Bushey; Karen Leeming, Wealdstone; Christopher Peter Moore, Rayners Lane, all of United Kingdom; Danielle Wettling, 71880 Chatenoy le Royal, France

[73] Assignee: Eastman Kodak Company, Rochester, N.Y.

[21] Appl. No.: 882,792

[22] Filed: Jun. 26, 1997

[30] Foreign Application Priority Data

Jul. 30, 1996 [GB] United Kingdom ............... 9615944

[51] Int. Cl.$^6$ ................................. A01N 25/26
[52] U.S. Cl. ............ 424/421; 424/405; 424/409; 424/411; 424/724; 514/63; 514/372; 514/373
[58] Field of Search .................. 424/421, 405, 424/406, 409, 411, 724; 514/63, 372, 373; 523/122

[56] References Cited

U.S. PATENT DOCUMENTS

| | | | |
|---|---|---|---|
| 2,038,694 | 4/1936 | Wiggins | 167/32 |
| 2,595,290 | 5/1952 | Quinn | 424/421 |
| 4,552,591 | 11/1985 | Millar | 106/18.33 |
| 4,959,268 | 9/1990 | Hagiwara et al. | 428/403 |
| 5,651,978 | 7/1997 | Tomtoka et al. | 434/421 |

FOREIGN PATENT DOCUMENTS

| | | |
|---|---|---|
| 190504 | 8/1986 | European Pat. Off. |
| 200605 | 3/1996 | European Pat. Off. |
| 96-420086 | 3/1996 | European Pat. Off. |
| 96-200601 | 9/1996 | European Pat. Off. |
| 2710628 | 4/1995 | France |

Primary Examiner—Neil S. Levy
Attorney, Agent, or Firm—John R. Everett

[57] ABSTRACT

A biocidal material comprises a biocide immobilized in a porous inorganic polymer network such as a sol-gel matrix. The polymer may be coated on an inorganic support. The material can be used for inhibiting microbial growth in an aqueous medium, e.g., the wash solution of a photoprocessing system. The material can be housed in a flow-through container.

8 Claims, 6 Drawing Sheets

MATERIAL METHOD AND APPARATUS FOR INHIBITING MICROBIAL GROWTH IN AN AQUEOUS MEDIUM

CROSS REFERENCE TO RELATED APPLICATION

Reference is made to and priority claimed from Great Britain Application No. 961S994.7, filed Jul. 30, 1996.

FIELD OF THE INVENTION

The invention relates to a material, method and apparatus for inhibiting microbial growth in an aqueous medium.

BACKGROUND OF THE INVENTION

Microbial growth occurs in many systems in which aqueous media such as water, aqueous solutions and aqueous dispersions are employed.

For example, significant biofouling can occur in many areas of photoprocessing systems and, in particular, where low-flow rate washes and water recycling is used. The problem may be overcome by adding biocides to the wash water tanks when bacterial biofilm formation becomes evident visually. However at this point the biocides may not work and even at quite high concentrations are not particularly effective because the bacteria have attached to surfaces to form colonies that have built up in layers. Hence, any biocide in solution can only reach the outer biofilm layer and not the inner layers of the biofilm that are protected. Furthermore, widespread use of such biocides is not desirable because they are relatively expensive and require specialized disposal to protect the environment.

Alternative methods of inhibiting bacterial growth in aqueous media involve the gradual release of a biocide through interaction with water, e.g., by leaching.

U.S. Pat. No. 4,552,591 describes a biocidal composition for inhibiting microbial growth in oil field waters that comprises a biocide and a solid, particulate adsorbent therefor. The biocides are conventional water soluble compounds traditionally used in the treatment of oil field waters, e.g., 2-methyl-4-isothiazolin-3-one which are adhered to a known adsorbent e.g., diatomaceous earth. The compositions avoid the personal and environmental contamination which can result from spillage of the biocide used previously in liquid form. After addition to oil field waters, such compositions release the biocide through leaching.

A problem associated with the prior art methods and materials for inhibiting bacterial growth in aqueous media using biocides is that biocide is released in the media.

Furthermore, there is a need for a method and materials in which the biocide is only used on demand when the bacteria are present. Methods and materials that reduce the exposure of operators to toxic biocides are also sought.

SUMMARY OF THE INVENTION

The invention provides a biocidal material comprising a biocide and an inorganic carrier that is a porous inorganic polymer network in which the biocide is immobilized.

The invention also provides a method for inhibiting bacterial growth in an aqueous medium comprising contacting the aqueous medium with a biocidal material comprising a biocide and an inorganic carrier that is a porous inorganic polymer network in which the biocide is immobilized.

The invention also provides apparatus for inhibiting bacterial growth in an aqueous medium comprising a container having fluid inlet means and fluid outlet means, the fluid inlet and fluid outlet means communicating with an inner chamber such that, when the apparatus is in use, fluid entering the inner chamber through the fluid inlet means flows through the inner chamber and leaves the container through the fluid outlet means, characterized in that-the inner chamber holds a biocidal material comprising a biocide and an inorganic carrier that is a porous inorganic polymer network in which the biocide is immobilized.

The invention removes the need for conventional dosing of biocides in solution, either directly or by gradual release, which has many drawbacks. The biocide is only used on demand when the bacteria are present. The direct exposure of operators to toxic biocides is minimized. The invention is able to utilize inexpensive, readily available inorganic supports.

DETAILED DESCRIPTION OF THE INVENTION

Figure 1:
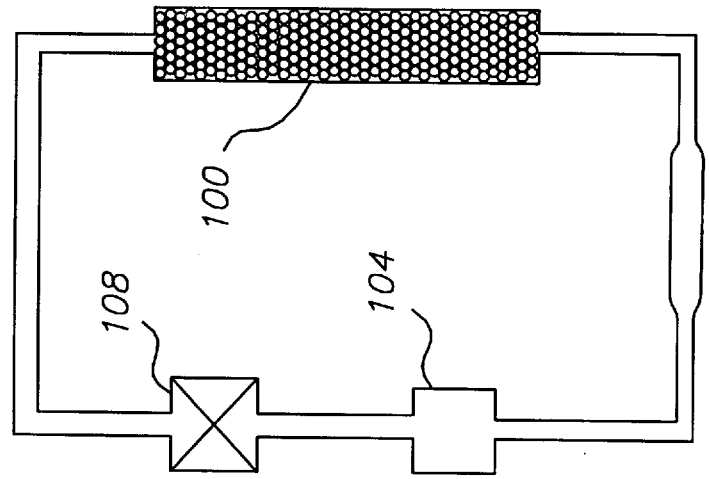
FIG. 1 is a schematic representation of apparatus used in evaluating the materials of the invention.
Figure 1:
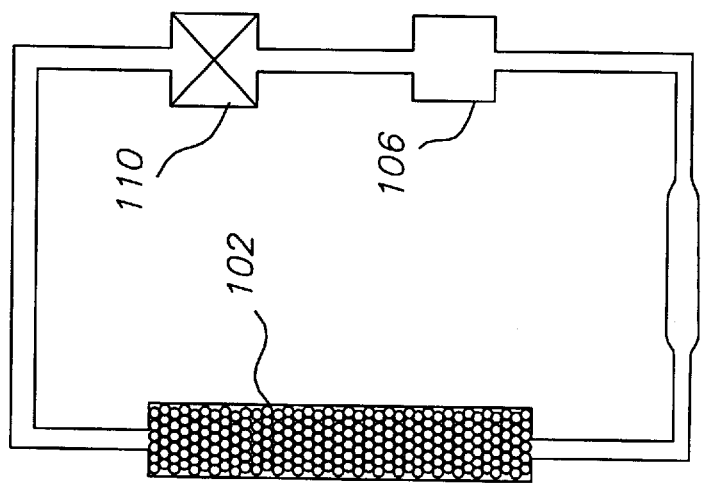

Suitable inorganic polymer carrier materials include those derived from sol-gel materials, silicon nitride, metal esters, e.g., acetates, nitrates, phosphates and ormosils (organically modified silicates).

Examples of suitable materials are referred to in "Sol-gel Science," by C. J. Brinker and G. W. Scherer, Academic Press, 1990, Chapters 2–3.

The preparation of inorganic, e.g., silica glasses through the low temperature "sol-gel" synthesis is known. For example, see Chem. Rev. 1990, 90, 33–72 "The Sol-Gel Process" by L. L. Hench and J. K. West.

An amorphous matrix of the glassy material may be prepared by the room temperature polymerization of suitable monomers, usually metal alkoxides. The polymerization of metal alkoxide mixtures results in a transparent porous solid (xerogel) with surface areas of up to hundreds of square meters per gram and having small pores, e.g., from 0.5 to 500 nm. The low temperature glass synthesis allows doping of the inorganic glass with organic molecules, e.g., a chemically sensitive dye.

The sol-gel glass has a cage-like porous molecular structure in which a single doping molecule can be isolated in an individual cage, even at high concentrations of additive. Molecules trapped in sol-gel glasses can interact with diffusible solutes or components in an adjacent liquid or gas phase in the pore space.

The sol-gel matrix may comprise one or more of $SiO_2$, $TiO_2$ and $ZrO_2$. In a preferred embodiment of the invention, a $SiO_2/TiO_2$ sol-gel matrix is used. Preferably, the mole ratio of Si:Ti in the sol-gel glass is from 90:10 to 50:50, more preferably from 80:20 to 60:40.

Suitable types of biocide include those described in "*Microbiocides for the Protection of Materials*", W. Paulus, published by Chapman Hall, 1993. They are agents capable of killing or inhibiting the multiplication of microorganisms such as bacteria, yeasts, fungi, algae and lichens. Examples include heterocyclic N,S compounds, compounds with activated halogen groups and quaternary ammonium salts.

Preferred biocides include those currently employed in the treatment of photoprocessing systems, e.g., isothiazolinones.

Examples of isothiazolinone biocides are those having the structure wherein

R represents hydrogen, alkyl, aryl, alkaryl and aralkyl; and, $R^1$ and $R^2$ independently represent hydrogen, halogen, alkyl, or $R^1$ and $R^2$ taken together represent the atoms necessary to complete a fused carbocyclic ring, preferably a 5- or 6-membered ring, e.g., a benzene ring.

Preferred biocides include those having the following structures:

wherein $R^3$ is an alkyl group having from 4 to 20 carbon atoms or an aryl group having from 6 to 20 carbon atoms;

wherein $R^5$ and $R^6$ are selected from hydrogen and halogen, and $R^4$ is an alkyl group having from 5 to 20 carbon atoms; and, wherein each of $R^7$, $R^8$ and $R^9$ is hydrogen or an alkyl group providing a total of from 2 to 20 carbon atoms; $R^{10}$ is substituted or unsubstituted alkyl or aryl, e.g., phenoxyethyl; and, Y is any suitable counter anion, e.g., halide.

Specific examples of commercially available isothiazolinone biocides include Proxel™ (manufactured by Zeneca):

Promexal™ (manufactured by Zeneca):

Kathon™ (manufactured by Rohm and Haas):

X = H,Cl

Other commercially available biocides are: Bronopol™ (manufactured by Boots):

Domiphen™ bromide (manufactured by Ciba-Geigy):

Vantocil™ (manufactured by Zeneca):

HCl (n = 12)

Densil S™ (manufactured by Zeneca):

Biocides which are hydrophobically modified Proxel™ and Kathon™ have been prepared having the following structures:

$R^3$=—$(CH_2)_7CH_3$ (Compound 1)

$R^3$=—$(CH_2)_{15}CH_3$ (Compound 2)

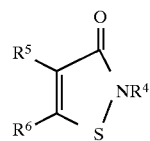

$R^4$=—$(CH_2)_7CH_3$, $R^5$=H, $R^6$=Cl (Compound 3)
$R^4$=—$(CH_2)_{17}CH_3$, $R^5$=H, $R^6$=Cl (Compound 4)
$R^4$=—$(CH_2)_7CH_3$, $R^5$=H, $R^6$=H (Compound 5)
$R^4$=—$(CH_2)_7CH_3$, $R^5$=Cl, $R^6$=Cl (Compound 6)

Many commercially available biocides are soluble in aqueous media and an increase in their hydrophobicity is required to convert them into the preferred hydrophobic compounds for use in the invention.

It is preferred that the biocides having a log P of at least 1.5 wherein P represents the partition coefficient between n-octanol and water defined as follows $$P = \frac{[\text{biocide}]_{octanol}}{[\text{biocide}]_{water}}$$

Log P is a well-known term used in literature on biocides. As used herein, it provides a measure of the hydrophobicity of the biocide.

A variety of commercial and hydrophobically-modified biocides have been studied. Partition coefficients between octanol and water have been determined at 25° C. by UV/visible absorption. First, the calibration curve of each biocide was determined as optical density ($OD_{abs}$) versus concentration of biocide in μg/g (ppm) of water for the predominantly water-soluble materials and μg/g of octanol for the predominantly oil-soluble biocides.

A known amount of biocide was placed in a glass vessel containing either 10 ml of water or 10 ml of octanol depending on the solubility of the biocide. An equal volume of the other solvent was added and the glass vessel sealed. The vessel was shaken vigorously for a few minutes and then every few hours for more than 48 hours. Each mixture was placed in a sealed separating funnel and left for a further 24 hours. The water phase of each mixture was removed and the UV/visible spectra run against water with appropriate dilutions to bring absorbance between 0 and 1.5 for the commercial biocides and the octanol fractions were examined for the hydrophobically modified biocides.

The following partition coefficients shown in Table 1 were determined.

TABLE 1

| Biocide | P |
|---|---|
| Promexal ™ | ~4.5 |
| Vantocil ™ | ~0.3 |
| Domiphen ™ | ~50 |
| Kathon ™ | ~1 |
| Proxel ™ | ~0* |
| Compound 1 | >330 |
| Compound 3 | >560 |
| Compound 2 | >130 |
| Compound 4 | >480 |

*i.e. there was almost no biocide in the oil phase.

The log P value of the biocides that are used in the invention is preferably at least 1.5, more preferably at least 2.0.

Preferably, the amount of biocide used is from 5 to 35 mole percent, more preferably from 20 to 30 mole percent based on the metal alkoxide or other precursor used to construct the inorganic polymer network.

Preferably, the inorganic polymer carrier is coated on a support. Preferred support materials are those to which the inorganic polymer readily adheres.

Inorganic support materials are advantageous. Many provide the additional benefits of low cost and physical robustness. Suitable materials include pumice, clay, sand, gravel, chalk, zeolites and glass. Such materials give the further advantage of easy disposal and are potentially more stable over wide pH ranges than organic polymer-based systems.

Polymers suitable for use as support materials include any inert, water insoluble polymers having appropriate surface properties. Preferably, such polymer supports have a non-crystalline surface. Preferably, the polymer supports have a hydrophilic surface comprising groups such as —OH and —COOH.

Examples of suitable types of polymer from which suitable supports can be derived include ethenic polymers including polyolefins, polystyrene, polyvinyl chloride, polyvinyl acetate and acrylic polymers; and polymers formed by condensation reactions including polyesters, polyamides, polyurethanes, polyethers, epoxy resins, amino resins and phenol-aldehyde resins.

The support may take a variety of forms, e.g., particulate, sheet or fiber. It may be porous or non-porous.

The thickness of the inorganic polymer carrier coating on the support may be from 10 nm to 10 μm, preferably from 50 nm to 5 μm.

In accordance with one method of preparing a material of the invention, a solution of the biocide is made in an organic solvent, e.g., tetrahydrofuran or alcohol. The biocide solution is mixed with an alkoxide sol-gel forming pre-cursor. The pre-cursor containing the biocide may be coated on a support if required by any conventional coating means, e.g., dipping, spinning and spraying. The pre-cursor containing the biocide is left for some hours, e.g., from 4 to 6 hours, before removing the solvent, preferably under reduced pressure. Drying is preferably carried out in a vacuum oven at a temperature from 60° to 100° C.

In use, the aqueous medium is brought into contact with the biocidal material. Different ways of achieving contact include passing the aqueous medium through a container, e.g., a column containing the material in particulate form, passing the aqueous medium through a filter of the material and passing the aqueous medium over the material in the form of a surface coating.

The invention is of particular use in photoprocessing systems. Such systems comprise stages for developing, fixing, bleaching and washing an exposed photographic material. Each stage requires apparatus for applying the appropriate aqueous processing solution to the photographic material. The apparatus may comprise means for supplying, removing and, possibly, recirculating such solutions.

Particularly, the method of the invention may be used to inhibit microbial growth in the wash solution or other solutions used in a photoprocessor.

Figure 6:
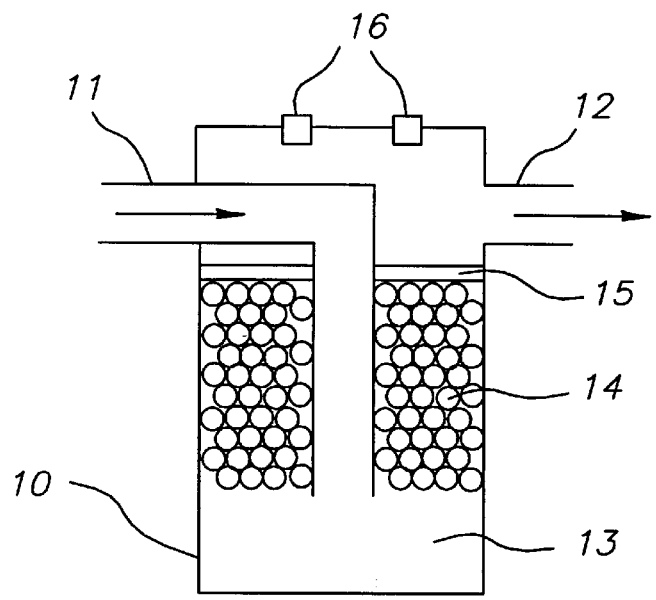
FIG. 6 is a schematic representation of apparatus for use in performing the method of the invention.

FIG. 6 is a schematic representation of apparatus for use in performing the method of the invention. The apparatus comprises a container 10 having fluid inlet means 11 and fluid outlet means 12 said inlet and outlet means 11, 12 communicating with an inner chamber 13 of the container. When the apparatus is in use, fluid entering the inner chamber through the inlet means 11 flows through the chamber 13 and leaves the container through the outlet means 12. The inner chamber 13 holds a biocidal material in accordance with the invention in the form of particles 14. A filter 15 to retain the particles is positioned at the top of the inner chamber to prevent loss of the particles from the device. The top of the container 10 is provided with plugs 16 for venting any gas that accumulates in the device.

Fluid entering the device flows down a central tube and subsequently flows up through the particles. The arrows indicate the direction of the flow of fluid through the device.

Figure 7:
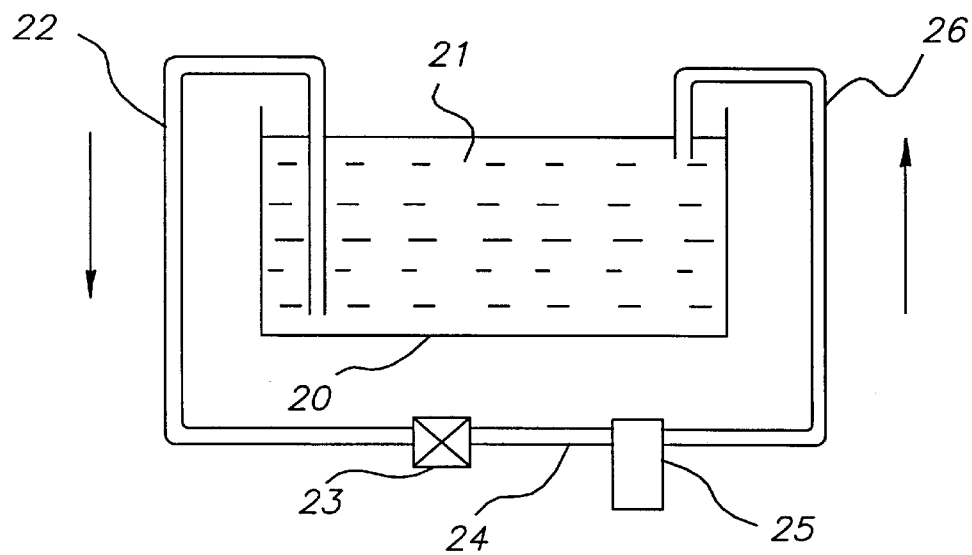
FIG. 7 is a schematic representation of the use of the apparatus shown in FIG. 4.

FIG. 7 is a schematic representation of the use of the apparatus shown in FIG. 6. A tank 20 containing water 21 is shown, e.g., the wash water tank of a photoprocessor. Tubing 22 has an open end in the water 21 at the bottom of tank 20, the other end being connected to the inlet of a pump 23 outside the tank 20. Tubing 24 connects the outlet of the pump 23 to the inlet of a device 25 of the type shown in FIG. 6. One end of tubing 26 is connected to the outlet of device 25 and the other end opens into the top of tank 20.

In use, water is pumped from the bottom of tank 20 through device 25 and back into tank 20 in a recirculation loop. The arrows indicate the direction of the flow of water around the loop.

The invention is further illustrated by way of example as follows.

Preparation of Biocide

A Proxel™ analogue (Compound 2) was prepared in three steps from commercially available starting materials as outlined in Scheme 1.

adapters and polypropylene nozzles. A nylon mesh filter was put at the bottom and top of each column in between two rubber washers. The columns, all silicone rubber tubing, flasks and nutrient broth necessary to complete the flow circuit were sterilized by autoclaving at 120° C. for >20 minutes. Each column was placed in circuit with 50 ml of nutrient broth as shown in FIG. 1. A shaking water bath held at 30° C. was used to keep the 250 ml wide-neck round-bottomed flasks containing the culture at this constant temperature. A small inoculum of pre-prepared bacterial culture was added to each flask to give a known number of bacteria/ml in the flask. At time zero, a small aliquot of the bacterial culture was removed from each flask for further counting/analysis and the pumps started to give a volume flowrate of 13.5 ml/min. The flow direction was upwards through the stones.

Figure 2:
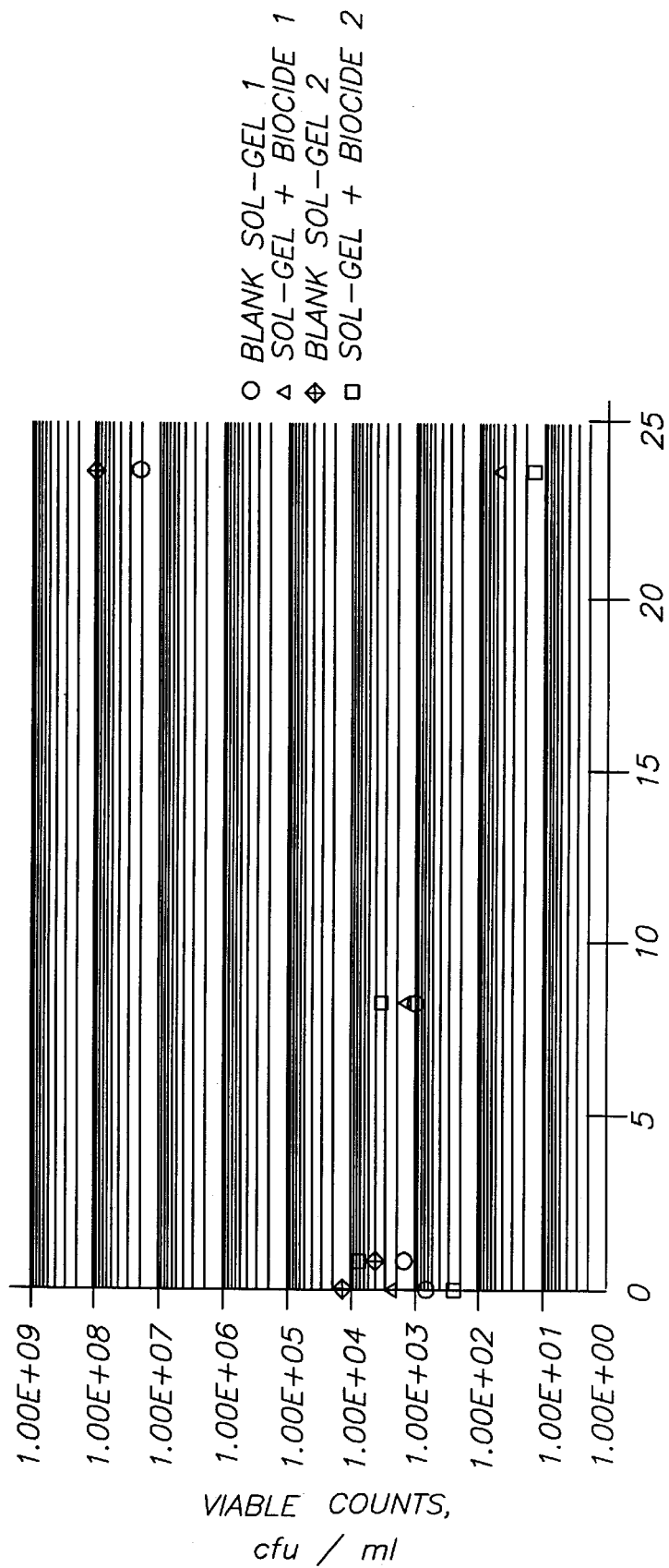
FIG. 2 is a graphical representation of results achieved using the invention in accordance with Example 1 described below.

Aliquots were removed from the reaction flask at time intervals of 0.5, 8 and 24 hours and the viable counts performed. These data are summarized in FIG. 2. There is the usual lag phase as the bacteria become accustomed to the new medium, followed by a growth phase in each system. However, it is quite evident that the bacterial population is significantly lower in the active system, which shows a bactericidal effect compared to the control.

Differences could be seen visually between the active and control systems since solutions become more cloudy as bacterial populations increase due to light-scattering phe-

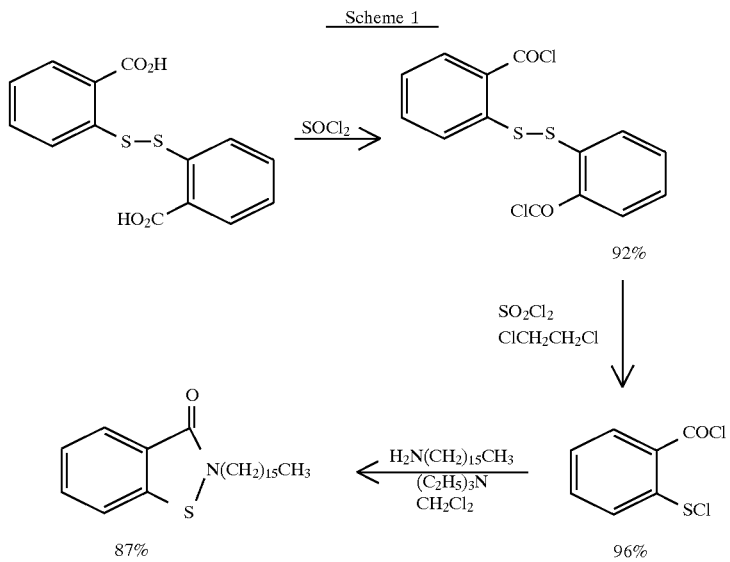

Scheme 1

EXAMPLE 1

Compound 2, dissolved in a small quantity of tetrahydrofuran (THF), was added at 25% mol/mol to a 70/30 Si/Ti alkoxide sol-gel forming precursor ("liquid-coat," Merck ZLI 2132,1857). The mixture was coated onto pumice stones (Prolabo 26398293), leaving the sol in contact with the support for about 5 hours before removing the solvent under reduced pressure (14 mm Hg) and drying in a vacuum oven. Analysis (IR, MS and elemental) of dried samples showed the presence of immobilized biocide.

Control (blank sol-gel) and active (immobilized bioeide in sol-gel) coated pumice stones were tested in a nutrient broth containing ~$10^4$ bacteria/ml (*Pseudomonas aeruginosa*). The control particles and active particles were each put separately into a 10 cm glass column with screw-tight plastic nomena. Light scattering and perhaps UV absorption could be used to detect total number of bacteria; but, unlike plating, these techniques would not distinguish between viable and non-viable organisms.

In addition, the solutions were analyzed after the experiment. None of the Compound 2 or obvious metabolites were detected by HPLC or mass spectrometry.

EXAMPLE 2

Figure 3:
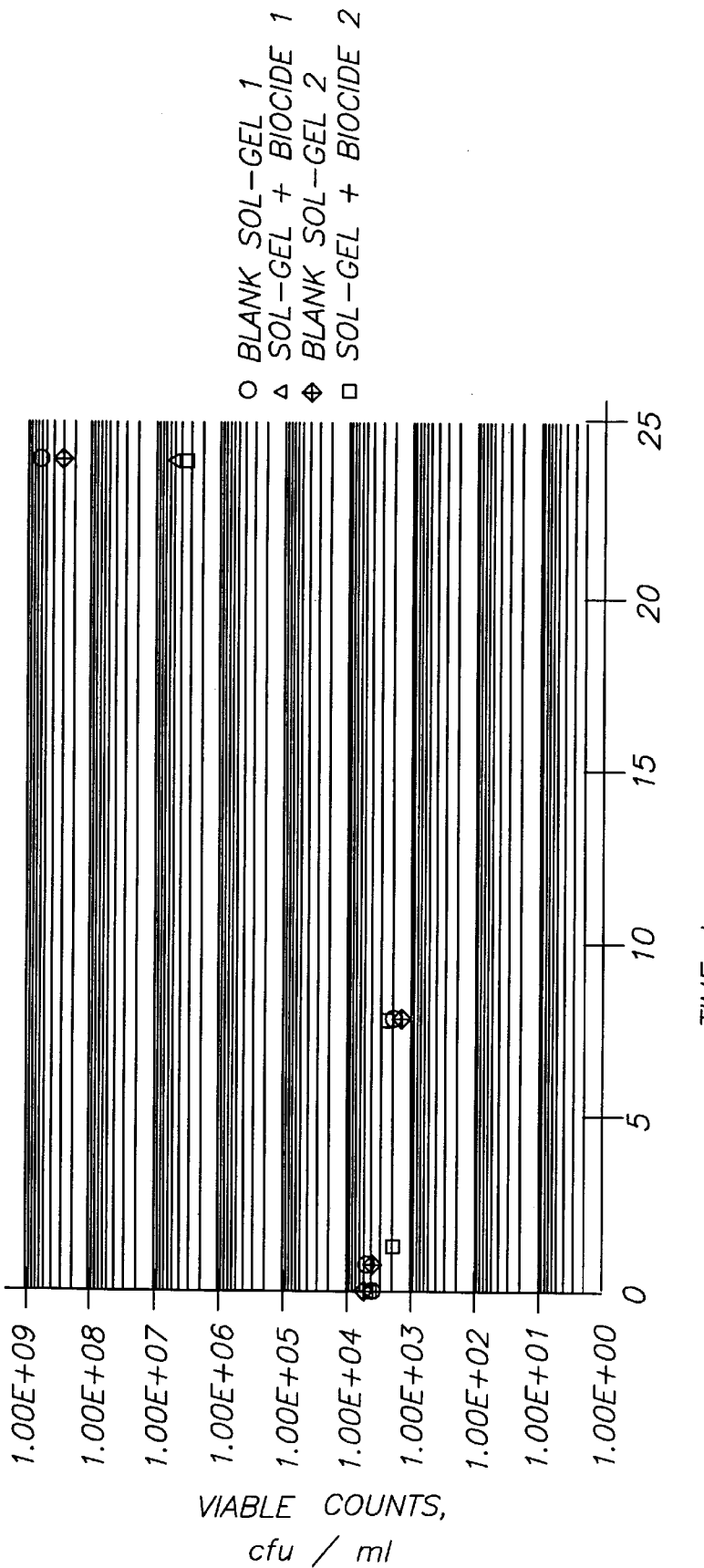
FIG. 3 is a graphical representation of results achieved using the invention in accordance with Example 2 described below.

An identical method to Example 1 was used except that porous clay beads (OBI, 8–16 mm) were used in place of the pumice stones. Microbiological evaluation was carried out in a similar fashion to Example 1, and the data is given in FIG. 3. This demonstrates that bacteriostatic activity is obtained for the Compound 2 immobilized in sol-gel coated on clay beads.

EXAMPLE 3

Figure 4:
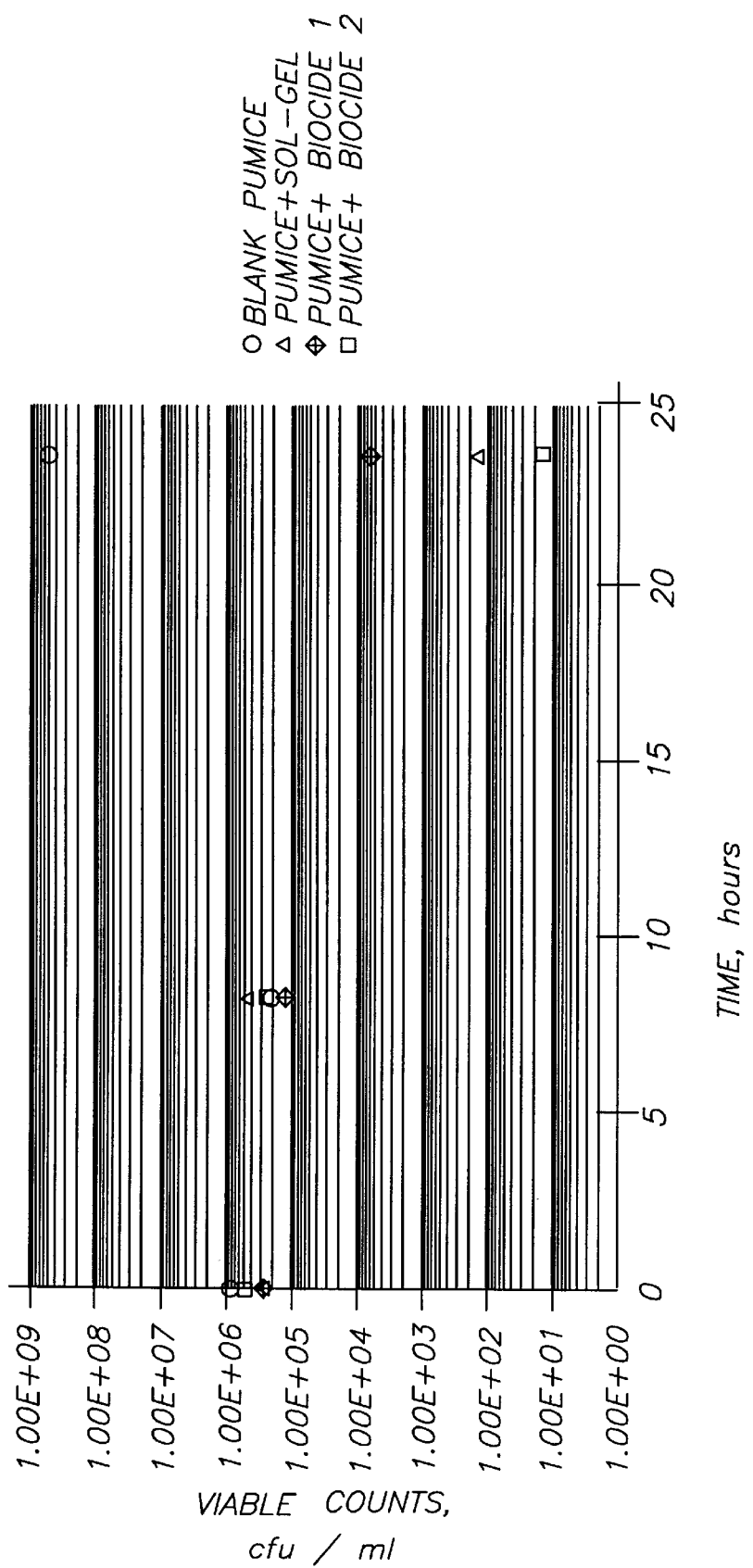
FIG. 4 is a graphical representation of results achieved using the invention in accordance with Example 3 described below.

An identical method to Example 1 was used except that Compound 3 was used in place of Compound 2. Microbiological evaluation was carried out in a similar fashion to Example 1, using untreated pumice stones (no sol-gel coating) and those having a sol-gel coating only (no biocide); the data are given in FIG. 4.

The data demonstrate that the biocidal activity of the hydrophobic biocide is maintained using immobilization in sol-gel coated onto pumice stones.

EXAMPLE 4

Figure 5:
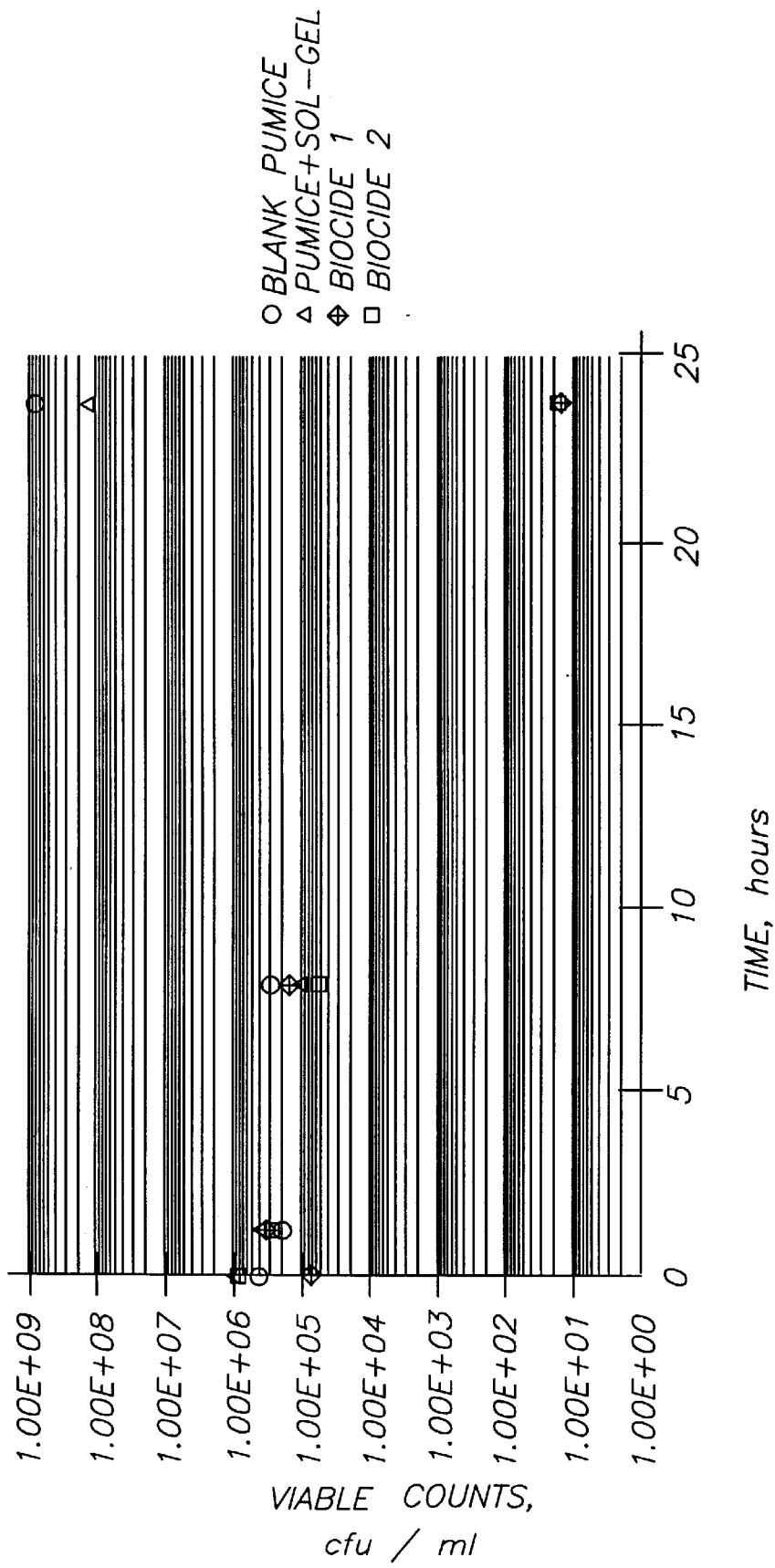
FIG. 5 is a graphical representation of results achieved using the invention in accordance with Example 4 described below.

An identical method to Example 1 was used except that Compound 3 was used in place of Compound 2. The resultant active and control pumice stones were dried for 1 hour at 90° C. and tested as described previously. The microbiological results in FIG. 5 show that the drying treatment has removed any contribution from the blank sol-gel coating. In this case Compound 3 immobilized in sol-gel coated on pumice stones is strongly bactericidal.

The invention has been described in detail with particular reference to certain preferred embodiments thereof, but it will be understood that variations and modifications can be effected within the spirit and scope of the invention.

We claim:

1. A biocidal material comprising a biocide and an inorganic carrier that is a porous $SiO_2/TiO_2$ sol-gel matrix in which the biocide is immobilized.

2. The material of claim 1 wherein the mole ratio of Si:Ti in said sol-gel matrix is from 80:20 to 60:40.

3. The material of claim 1 wherein said biocide has the structure

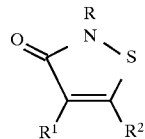

wherein

R represents hydrogen, alkyl, aryl, alkaryl and aralkyl; and, $R^1$ and $R^2$ independently represent hydrogen, halogen, alkyl, or $R^1$ and $R^2$ taken together represent the atoms necessary to complete a fused carbocyclic ring.

4. The material of claim 1 wherein said inorganic polymer network is coated on a support.

5. The material of claim 4 wherein said support is an inorganic support.

6. The material of claim 4 wherein said support is a particulate support.

7. A method for inhibiting microbial growth in an aqueous medium comprising contacting said aqueous medium with the biocidal material of claim 1.

8. The method of claim 7 wherein said aqueous medium is a wash solution of a photoprocessing system.

* * * * *